(12) United States Patent
Kraus

(10) Patent No.: US 8,632,571 B2
(45) Date of Patent: Jan. 21, 2014

(54) PEDICLE SCREW AND DEVICE AND METHOD FOR STABILIZING THE SPINAL COLUMN

(71) Applicant: Kilian Kraus, Werneck (DE)

(72) Inventor: Kilian Kraus, Werneck (DE)

( * ) Notice: Subject to any disclaimer, the term of this patent is extended or adjusted under 35 U.S.C. 154(b) by 0 days.

(21) Appl. No.: 13/662,671

(22) Filed: Oct. 29, 2012

(65) Prior Publication Data

US 2013/0226243 A1    Aug. 29, 2013

Related U.S. Application Data

(63) Continuation of application No. PCT/EP2011/056696, filed on Apr. 28, 2011.

(30) Foreign Application Priority Data

Apr. 30, 2010    (DE) .......................... 10 2010 028 423

(51) Int. Cl.
*A61B 17/70*    (2006.01)
(52) U.S. Cl.
USPC ............ 606/264; 606/265; 606/267; 606/300
(58) Field of Classification Search
USPC .......................... 606/246, 264–277, 300–321
See application file for complete search history.

(56) References Cited

U.S. PATENT DOCUMENTS

| 8,048,133 B2 | 11/2011 | Biedermann et al. |
| 2006/0200131 A1 | 9/2006 | Chao et al. |
| 2008/0177260 A1 | 7/2008 | McKinley et al. |
| 2008/0195159 A1 | 8/2008 | Kloss et al. |
| 2009/0312804 A1 | 12/2009 | Gamache et al. |
| 2010/0234891 A1 | 9/2010 | Freeman et al. |

FOREIGN PATENT DOCUMENTS

| DE | 102005005647 A1 | 8/2006 |
| EP | 1774919 A1 | 4/2007 |
| WO | 2008089096 A2 | 7/2008 |
| WO | 2009029928 A1 | 3/2009 |
| WO | 2009106733 A2 | 9/2009 |

*Primary Examiner* — Mary Hoffman
*Assistant Examiner* — Christina Negrellirodriguez
(74) *Attorney, Agent, or Firm* — Laurence A. Greenberg; Werner H. Stemer; Ralph E. Locher

(57) ABSTRACT

A pedicle screw has a screw shaft and a screw head connected thereto. The screw head has a center longitudinal axis extending in an X-direction. The screw further has a recess for receiving a connecting rod with a circular cross-section, a fixing screw that is used to fix the connecting rod in the screw head, a clamping unit between the fixing screw and a head base and an intermediate element.

19 Claims, 9 Drawing Sheets

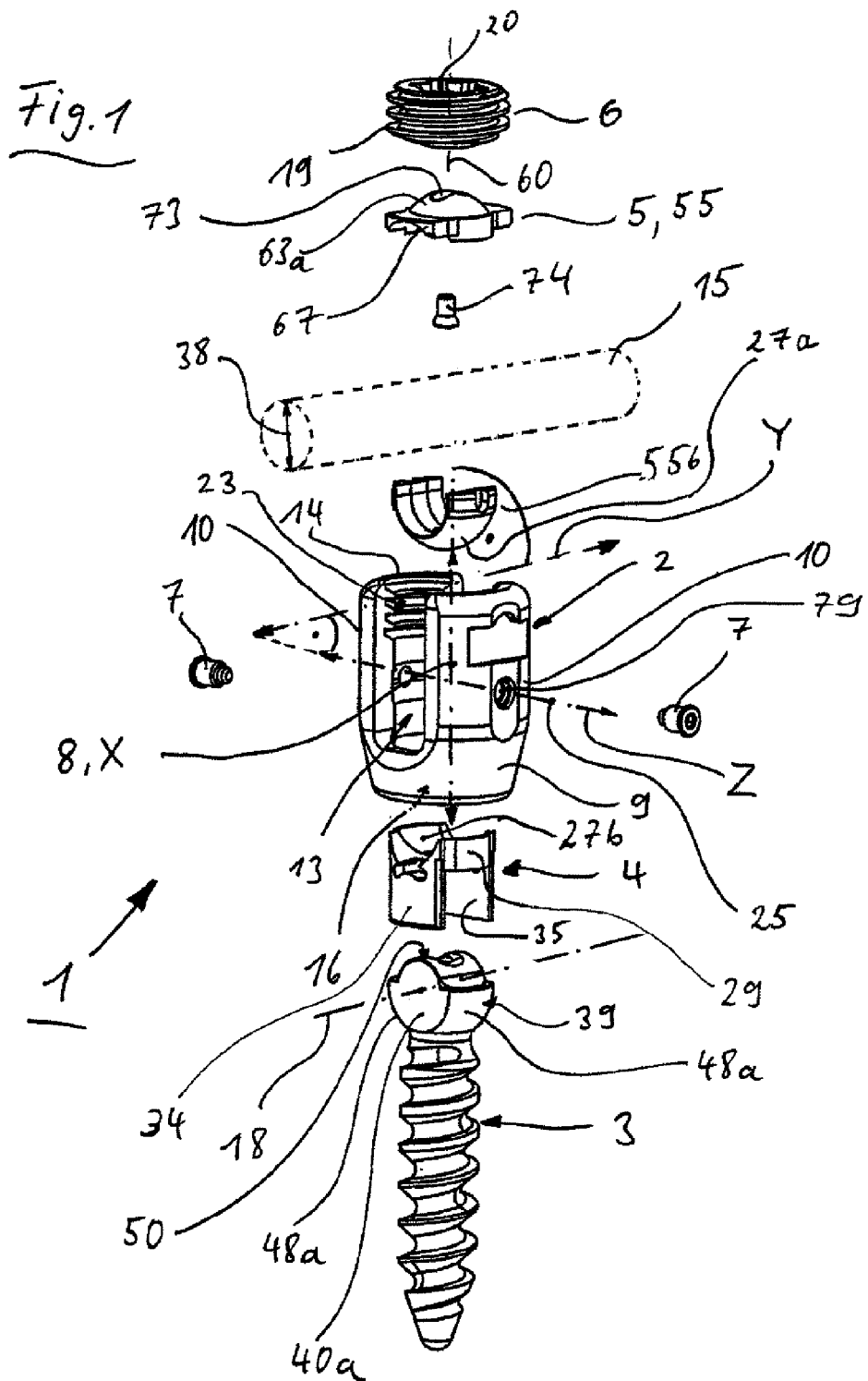

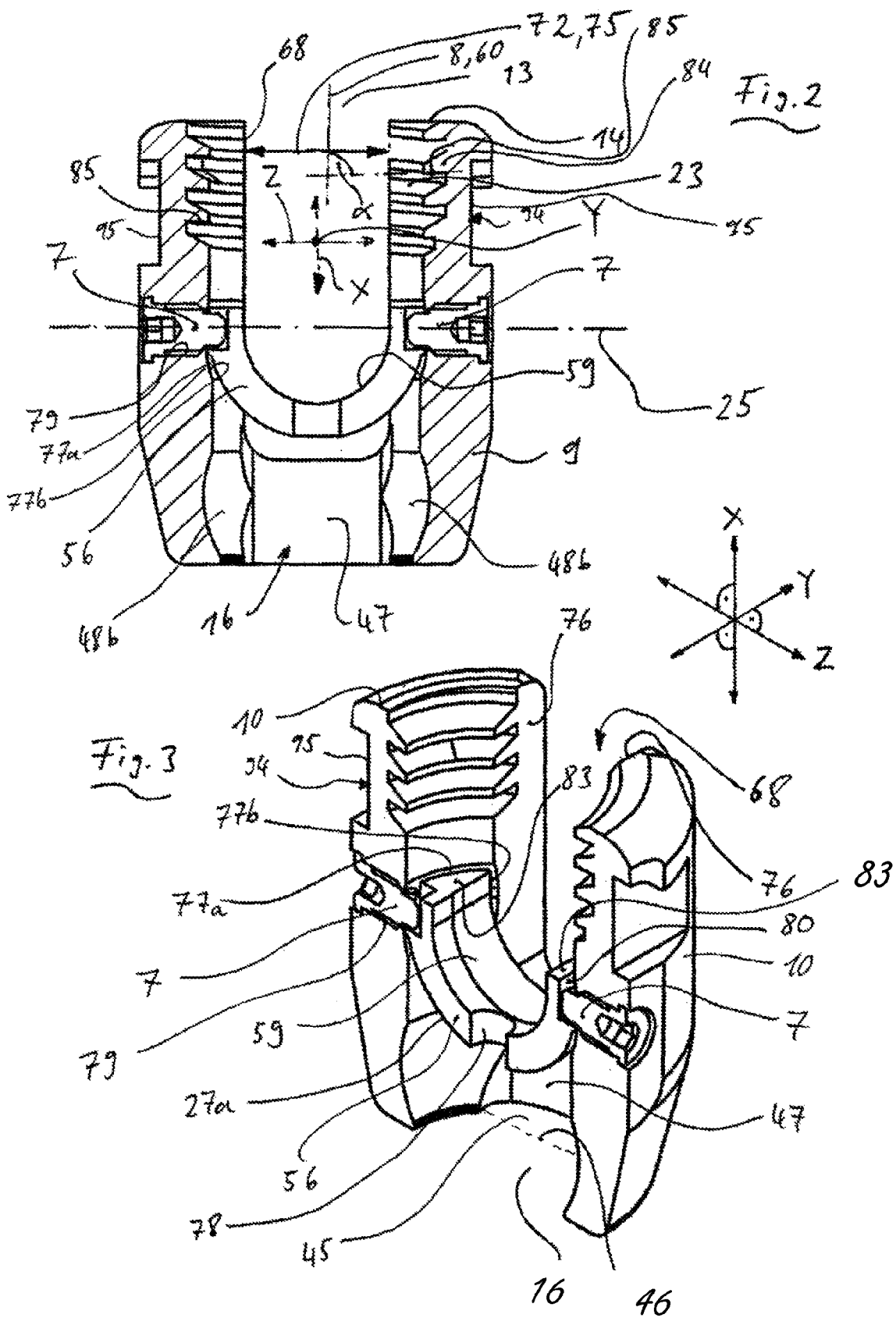

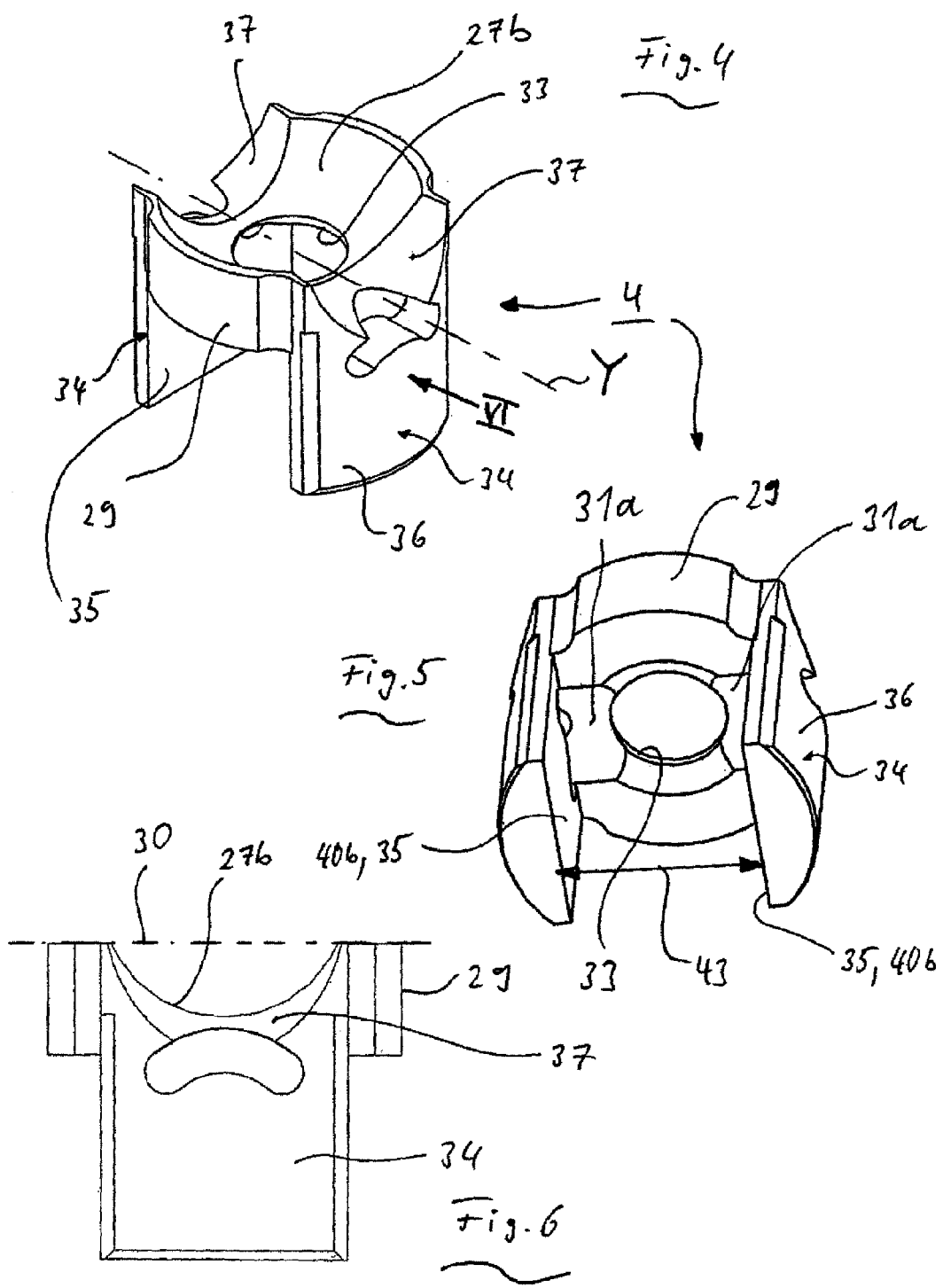

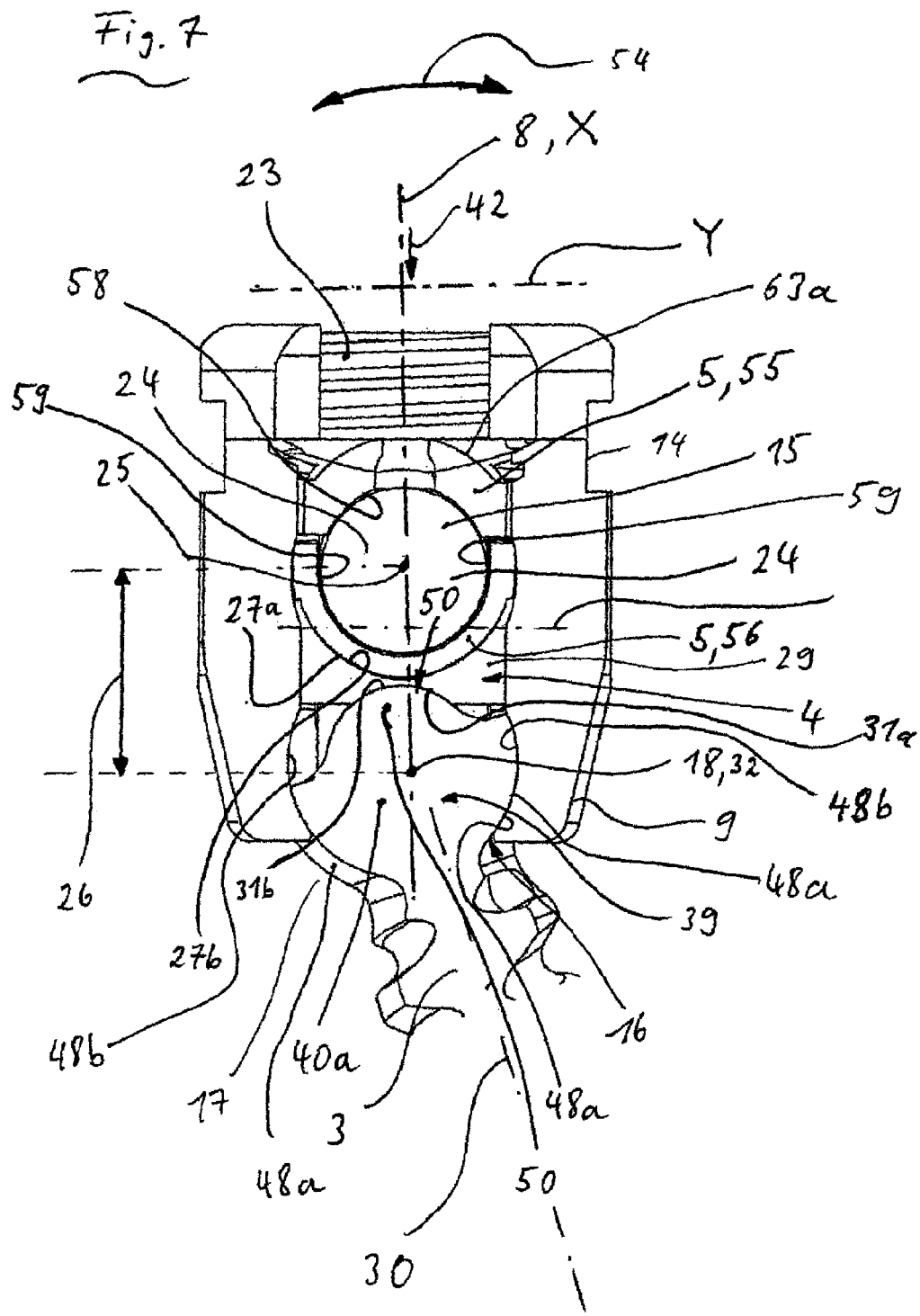

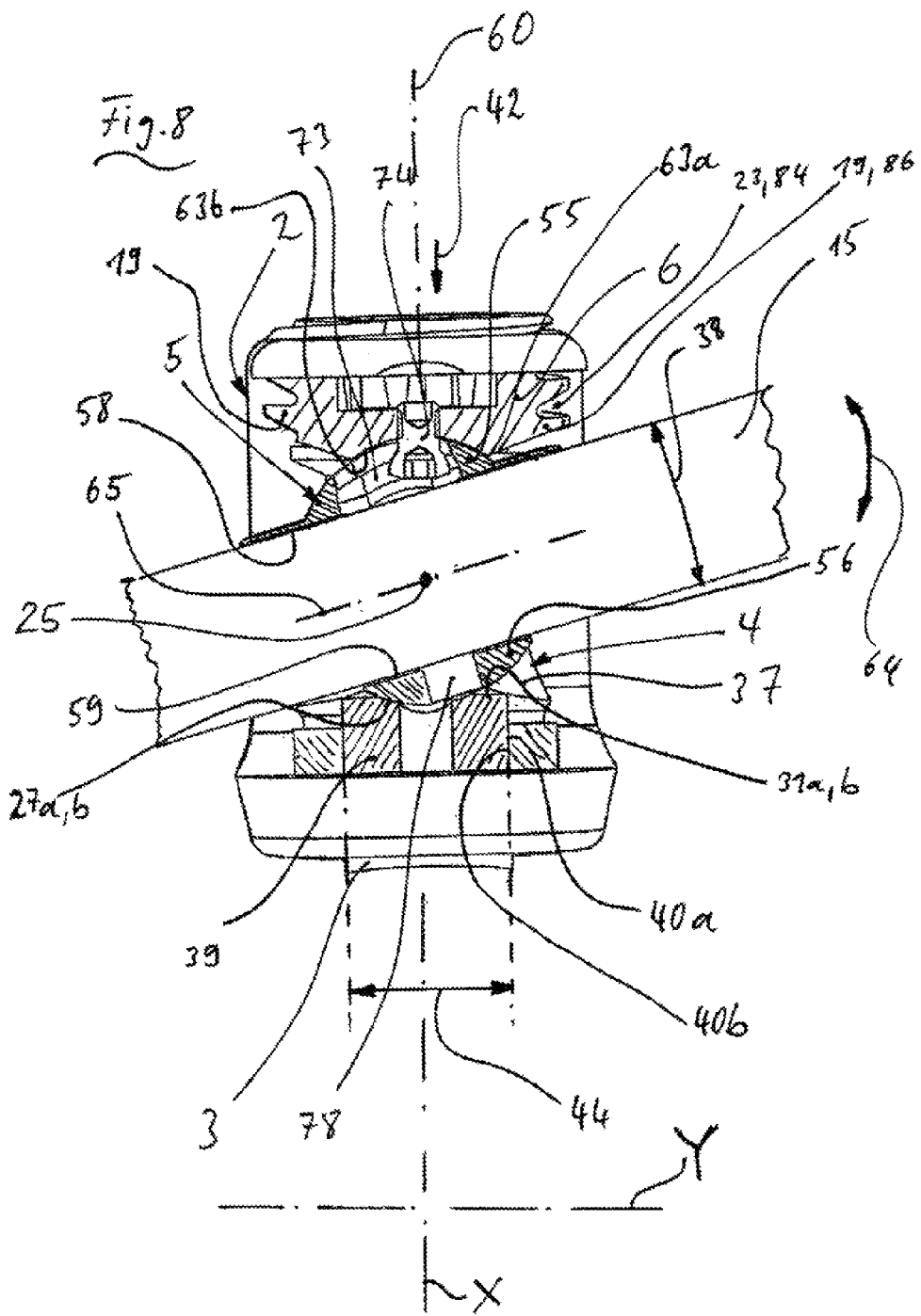

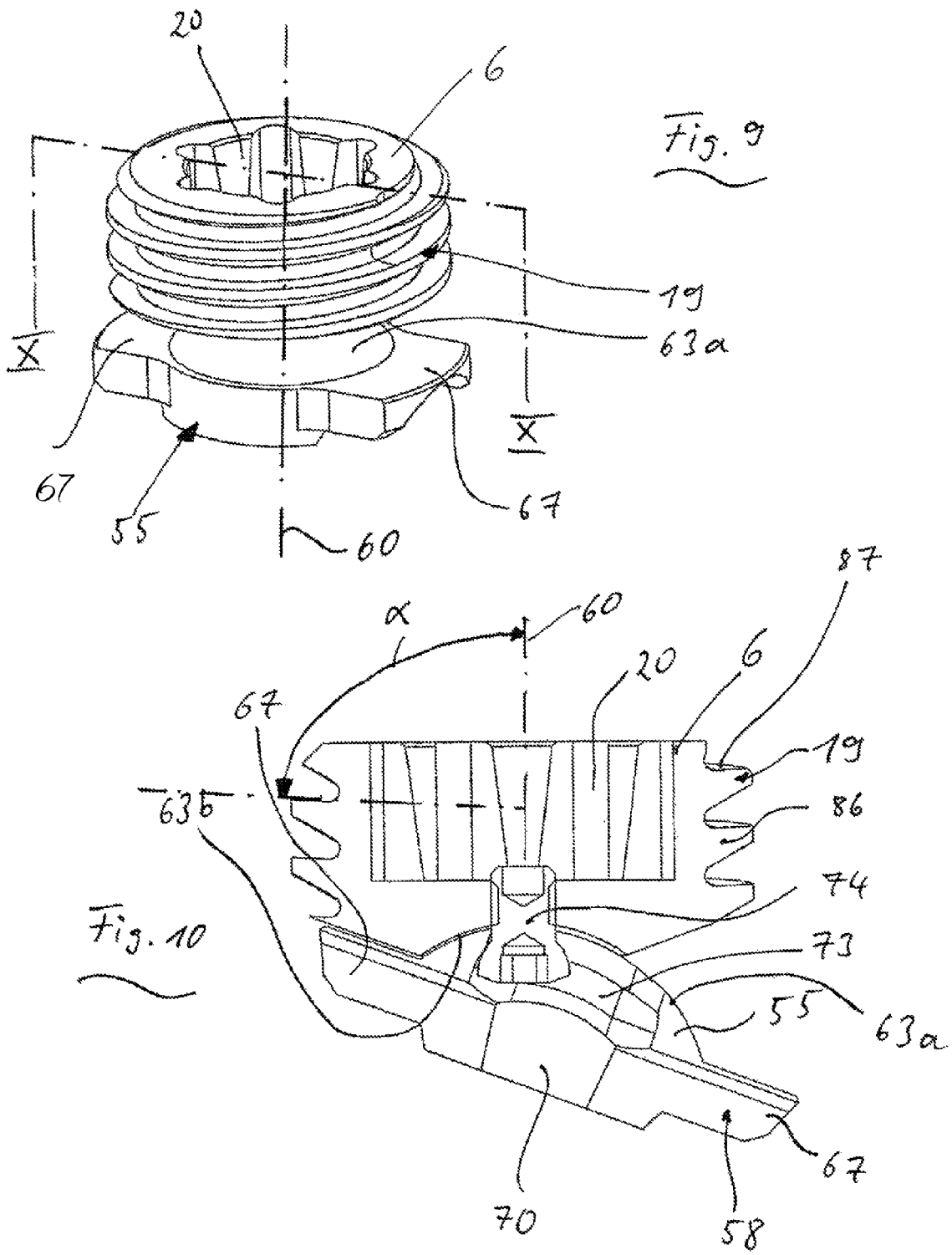

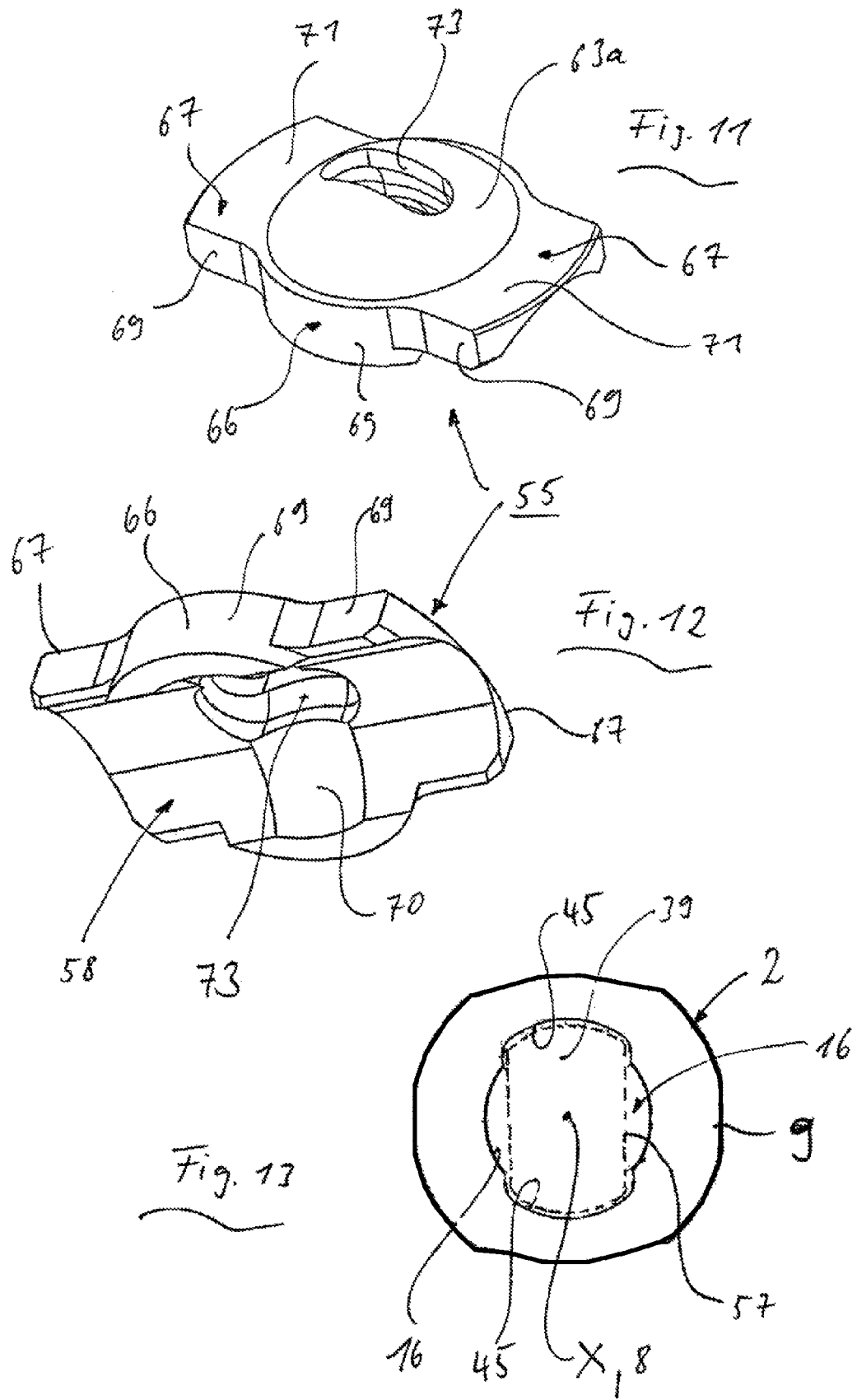

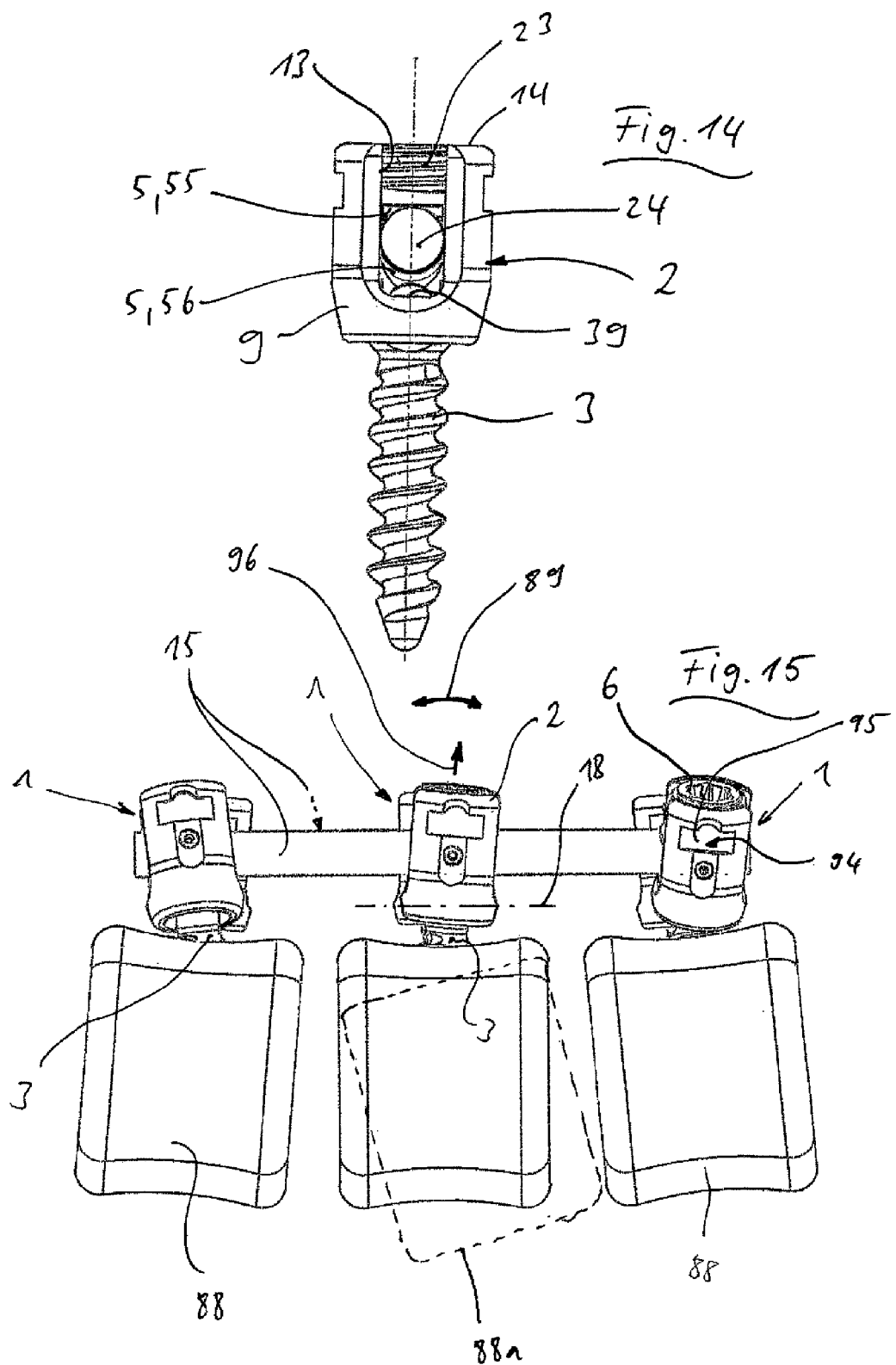

PEDICLE SCREW AND DEVICE AND METHOD FOR STABILIZING THE SPINAL COLUMN

CROSS-REFERENCE TO RELATED APPLICATION

This application is a continuation, under 35 U.S.C. §120, of copending international application No. PCT/EP2011/056696, filed Apr. 28, 2011, which designated the United States; this application also claims the priority, under 35 U.S.C. §119, of German patent application No. DE 10 2010 028 423.8, filed Apr. 30, 2010; the prior applications are herewith incorporated by reference in their entireties.

BACKGROUND OF THE INVENTION

Field of the Invention

The invention relates to a pedicle screw and to a device for stabilizing the spinal column. Such a device is used, for example, when a vertebra that is no longer functional, for example on account of an intervertebral disk defect, is to be fixed to adjacent vertebrae. In these cases, two rods having a circular cross-sectional shape, hereinafter called connection rods, are in most cases secured to the vertebrae in question with the aid of what are called pedicle screws, with a lateral spacing being maintained between them. The pedicle screws have a screw shank and a screw head. At its lower end directed toward the screw shank, the screw head has a head base, on which two wall portions are integrally formed that extend upward along the central longitudinal axis. The direction in which the central longitudinal axis of the head extends is referred to hereinbelow as the X-direction. The wall portions delimit a recess which passes through the screw head in a direction at right angles to the X-direction, namely a Y-direction, and which serves to receive a connection rod. The recess also opens out in the upper face of the head, and it is from there, for the purpose of fixing a connection rod, that a fixing screw with an outer thread is screwed into an inner thread of the wall portions. As regards the joining between the head and the screw shank, a distinction is made between monoaxial and polyaxial pedicle screws. In the former, the screw head is connected rigidly to the screw shank, in which case the screw shank extends in the direction of the central longitudinal axis of the screw head or in the X-direction. If screws of this kind are screwed into an incorrectly positioned vertebra, the latter can be easily repositioned with the aid of a tool applied to the screw head, i.e. can be brought to its normal position. A disadvantage of these screws is that, for example after repositioning of a vertebra, the pedicle screw is at an inclination relative to a connection rod, such that the latter extends correspondingly obliquely, and not straight or in the Y-direction, in the recess of the screw head and, consequently, cannot be reliably fixed therein. This situation is remedied by the polyaxial pedicle screws, in which screw head and screw shank are connected to each other via a ball joint. However, a disadvantage is that the polyaxial mobility of the head means that repositioning of a vertebra is not possible in the above-described manner. For this purpose, a mandrel is needed that is inserted into an axial opening present on the upper face of the screw shank. A compromise between the two types of screws is provided by a pedicle screw known from published, non-prosecuted German patent application DE 10 2005 0005 647 A1, in which the head is pivotable relative to the screw shank only about a single direction, the Y-direction, extending at right angles to the X-direction. The screw head can in this way be pivoted in relation to the Y-direction, or the longitudinal direction of a connection rod, for example in order to vary the distance between two connection rods. At the same time, however, the screw head can be acted on in the Y-direction, i.e. for example in the direction of the longitudinal extent of a connection rod for the purpose of repositioning a vertebra with the aid of a tool, since it is connected rigidly to the screw shank with respect to this direction. In the known screw, the pivotability of the connection rod in the recess of the screw head is ensured by a clamping device which is present there. The clamping device is subjected to a force by the abovementioned fixing screw and the clamping of the connection rod in the direction of the head base. This force has to be introduced into the screw shank, so that the articulated connection between the screw head and the screw shank is blocked and the screw head is fixed in the respective pivoting position. To ensure that the connection rod in the assembled state, i.e. with the fixing screw tightened, is held reliably and if appropriate for a very long period of time, the parts cooperating with each other should experience the least possible surface pressure, i.e. the force flow into the screw shank should take place via two surfaces that lie on each other over the greatest possible area. In the known pedicle screw, a spherical surface of the clamping device bears on a complementary spherical surface at the end of the screw shank. However, because of the pivotable bearing of the screw head on the screw shank, there is only one pivoting position in which the spherical surfaces cooperating with each other are concentric to each other. In all other pivoting positions of the head, this is not the case, such that there is a punctiform or any contact between the spherical surfaces. Reliable fixing of the connection rod is not provided in this case.

SUMMARY OF THE INVENTION

The object of the invention is to propose a pedicle screw and a device for stabilizing the spinal column, which is improved in this respect.

With the foregoing and other objects in view there is provided, in accordance with the invention a pedicle screw. The pedicle screw contains a screw shank and a screw head connected to the screw shank. The screw head has a central longitudinal axis extending in one direction, being an X-direction. The screw head further has an upper face, a lower end directed toward the screw shank, a head base disposed at the lower end and having a bottom opening, and two wall portions disposed on the head base and being integrally formed to extend away from the screw shank in the X-direction and laterally delimit a recess extending in a Y-direction at right angles to the X-direction and opens into the upper face of the screw head for receiving a connection rod with a circular cross-sectional shape. The wall portions each have an inner face with an inner thread. The screw shank has a joint head protruding through the bottom opening in the head base and into the recess and is mounted therein such that the screw head is pivotable relative to the screw shank about a single head pivot axis extending parallel to the Y-direction. The screw shank further has a mating cylindrical surface disposed on the joint head. A fixing screw fixes the connection rod in the screw head disposed in the recess and engages, with an outer thread, in the inner thread on the inner face of the wall portions. A clamping device is disposed between the fixing screw and the head base being held in the recess so as to be pivotable in the screw head about a pivot axis. The clamping device extends in a Z-direction at right angles to the Y-direction and X-direction and is disposed at a spacing in the X-direction above the single head pivot axis. The clamping device has a hollow space formed therein, through which the connection rod passes in an assembled state, and also a lower spherical surface directed toward the head base and the lower spherical surface has a sphere center lying on the pivot axis of the clamping device. The clamping device, in the assembled state, is subjected by the fixing screw to a force directed toward the head base. An intermediate element is disposed in the head base. The intermediate element has a first side directed toward the clamping device, a mating spherical surface disposed on the first side and cooperating with the lower spherical surface of the clamping device and, on a second side directed toward the screw shank, the intermediate element has a cylindrical surface cooperating with the mating cylindrical surface on the joint head. The cylindrical surface and the mating cylindrical surface have a common axis of curvature coincident with the single head pivot axis of the screw head.

The pedicle screw has the head base, the intermediate element which, on its side directed toward a clamping element, has a mating spherical surface cooperating with the lower spherical surface of the clamping device and, on its side directed toward the screw shank, has a cylindrical surface that cooperates with a mating cylindrical surface present on the joint head. The cylindrical surfaces have a common axis of curvature coincident with the pivot axis of the screw head. A configuration of this kind ensures that, in each pivoting position of the screw head, the force is introduced into the screw shank via a large area of contact between the parts concerned. Upon pivoting of the screw head, the common sphere center of the spherical surfaces and the common axis of curvature remain unchanged, such that a punctiform or linear mutual contact is avoided and reliable fixing of the connection rod is ensured in every pivoting position of the screw head.

Other features which are considered as characteristic for the invention are set forth in the appended claims.

Although the invention is illustrated and described herein as embodied in a pedicle screw and a device and method for stabilizing the spinal column, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 is a diagrammatic, perspective exploded view of a pedicle screw according to the invention;

FIG. 2 is a cross sectional view taken along the XZ plane indicated in FIG. 1;

FIG. 3 is a perspective view of the section shown in FIG. 2;

FIG. 4 is a diagrammatic, perspective view of an intermediate element;

FIG. 5 is a perspective view of the intermediate element in a position different from FIG. 4;

FIG. 6 is a side view in the direction of the arrow VI shown in FIG. 4;

FIG. 7 is a longitudinal sectional view through the pedicle screw, in which the screw head is pivoted relative to the screw shank;

FIG. 8 is a partial longitudinal sectional view through a screw head, with a connection rod held obliquely therein;

FIG. 9 is a perspective view of a fixing screw, with an upper clamping element fixed thereon;

FIG. 10 is a longitudinal sectional view taken along the line X-X shown in FIG. 9, wherein the upper clamping element is pivoted relative to the fixing screw;

FIG. 11 is a perspective view of the upper clamping element;

FIG. 12 is a perspective view of the upper clamping element in another position;

FIG. 13 is a plan view of the underside of the screw head;

FIG. 14 is a side view of a pedicle screw, in which the central longitudinal axis of the screw head and the central longitudinal axis of the screw shank lie on one line;

FIG. 15 is an illustration showing a device composed of two connection rods and of six pedicle screws and designed for stabilizing a spinal column.

DETAILED DESCRIPTION OF THE INVENTION

Figure 16:
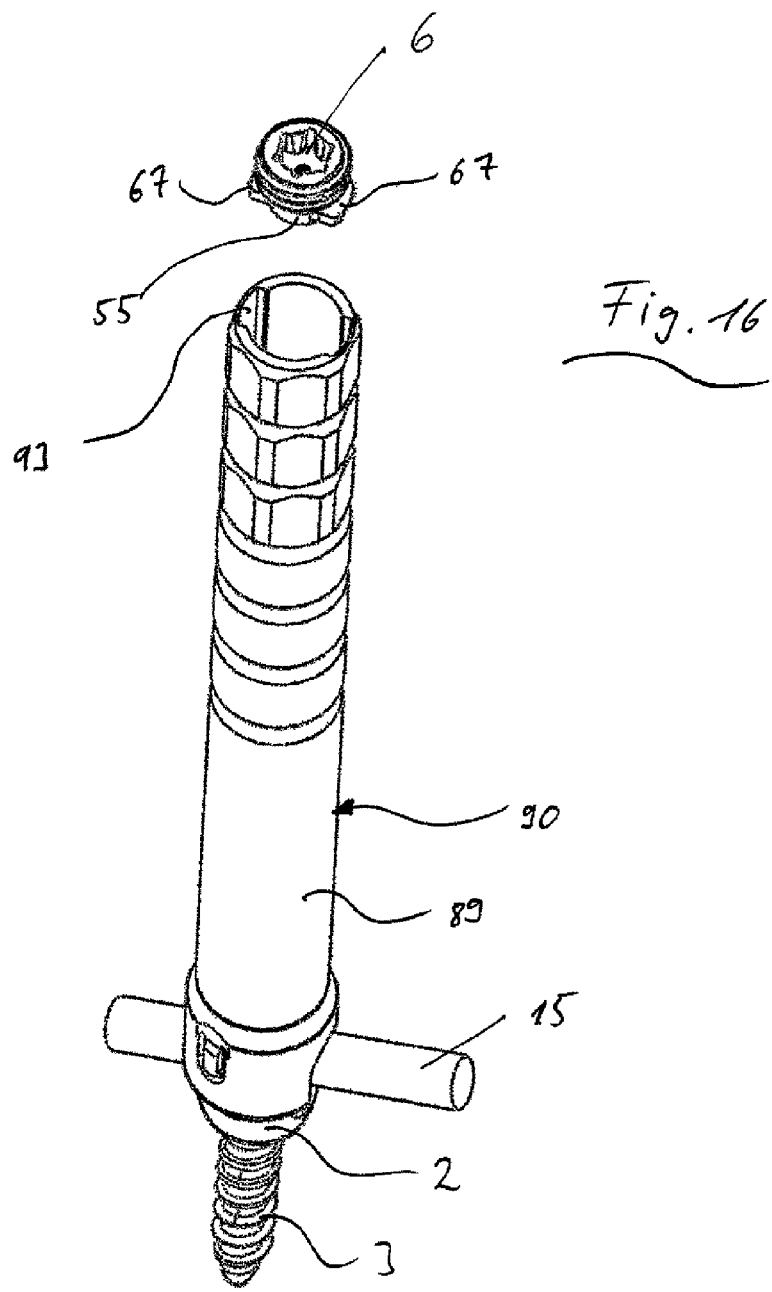
FIG. 16 is a perspective view of a screw with attached assembly tool.

Referring now to the figures of the drawing in detail and first, particularly, to FIG. 1 thereof, there is shown a pedicle screw according to the invention and composed principally of a screw head 2, a screw shank 3, an intermediate element 4, a clamping device 5, a fixing screw 6 and two bearing pins 7 for pivotably bearing the clamping device 5 in the screw head 2. The direction in which a central longitudinal axis 8 of the screw head 2 extends is designated herein below as the X-direction. At its lower end directed toward the screw shank 3, the screw head 2 has a head base 9, on which two wall portions 10 are integrally formed that extend upward, and away from the screw shank 3, in the X-direction. The wall portions 10 form a lateral boundary for a recess 13, which passes through the screw head 2 in the Y-direction and which opens into an upper face 14 of the head. The screw shank 3 protrudes through a bottom opening 16, which communicates with the recess 13, and its upper end arranged near the head and configured as a pivot head 39 extends into the head base 9 and is mounted therein such that the screw head 2 is pivotable relative to the screw shank 3 about a single head pivot axis 18 extending parallel to the Y-direction. The opening plane of the bottom opening 16 present in the head base 9 extends transversely with respect to the X-direction.

The fixing screw 6 is inserted into the recess 13 from the direction of the upper face 14 of the head. It has approximately the shape of a grub screw and contains an outer thread 19. In its end face directed away from the screw head 2, it has a recess 20 into which a non-illustrated rotation-imparting tool can be fitted. The outer thread 19 engages in an inner thread 23 present on the free ends of the wall portions 10. In the assembled state (FIGS. 7 and 8), the clamping device 5 is arranged between the fixing screw 6 and the head base 9 and has a hollow space 24, through which a circular cylindrical connection rod 15 passes. Moreover, the clamping device 5 is held in the screw head 2 such that it is pivotable about a pivot axis 25. The pivot axis 25 extends in the Z-direction, the latter being at right angles to the X-direction and Y-direction or at right angles to the plane spanned by these directions (the plane of the drawing in FIG. 7). In addition, the pivot axis 25 is arranged closer to the upper face 14 of the head 2 than is the head pivot axis 18, that is to say has a spacing 26 (FIG. 7) in the X-direction from the head pivot axis 18. The spacing 26 between the axes ensures that the connection rod 15 held by the clamping device 5 is able to pivot laterally with respect to the X-Z plane which contains the head pivot axis 18 and which, in FIG. 7, extends perpendicular to the plane of the paper. In this way, for example, the spacing between two connection rods 15 fixed next to each other on the spinal column can be changed. In the assembled state, the tightened fixing screw 6 subjects the clamping device 5 to a force directed to the head base 9. A lower spherical surface 27a present on the clamping device 5 is thus pressed against a complementary mating spherical surface 27b present on the intermediate element 4. The sphere centers of the spherical surfaces lie, at least in the assembled state, on the pivot axis 25 of the clamping device 5. This ensures that, irrespective of the pivoting position of the screw head 2, the surfaces are in full contact with each other. The mating spherical surface 27b is present on that side of the intermediate element 4 facing upward and toward the fixing screw 6.

The intermediate element 4 has an approximately disk-shaped base 29, of which a flat plane 30 (FIG. 6) extends, in the assembled state, parallel to the plane spanned by the Y-direction and Z-direction. The mating spherical surface 27b is present on the upper face of the base 29. A central opening 33 passes through the base 29 and makes assembly easier.

Laterally in the Y-direction, two wall portions 34 are formed integrally on the base 29 and extend downward in the X-direction and away from the base 29 toward the screw shank 3. Inner faces 35 of the wall portions 34 are flat, and they extend parallel to the X-direction and transverse to the Y-direction, i.e. they extend in the X-Z plane. Outer faces 36 of the wall portions 34 are curved radially outward with a contour shaped as an arc of a circle. The wall portions 34 are interrupted in the Y-direction by an opening 41, which serves to simplify production. Upper end faces 37 of the wall portions 34 extend obliquely downward and are parts of the jacket surface of an imaginary cylinder, of which the diameter corresponds to a diameter 38 of the connection rod 15. By beveled end faces 37, the pivoting range of a connection rod 15 in the recess 13 of the screw head 2 is increased, and the connection rod 15 bears on the end faces 37 in the respective pivoting end positions. The cylindrical surface 31a is arranged on the side directed toward the screw shank 3, or on the underside of the base 29, its axis of curvature 32 extending in the Z-direction (FIG. 7).

The joint head 39 has two diametrically opposite spherical surfaces 48a which cooperate, in the sense of a ball joint (FIG. 7), with complementary mating spherical surfaces 48b on the wall of the head base 9 surrounding the bottom opening 16. In addition, two flat surfaces 40a, which extend parallel to each other and parallel to the X-Z plane, are present on the joint head 39 and, in order to fix the joint head in terms of rotation about the central longitudinal axis 30 of the screw shank 2, cooperate with mating flat surfaces 40a. These could be present on the wall of the bottom opening 16. However, it is preferable that the mating flat surfaces 40b are formed by the inner faces 35 of the wall portions 34 of the intermediate element 4. A clearance 43 (FIG. 5) between the inner faces 35 of the wall portions 34 is slightly greater than a width 44 measured across the flat surfaces 40a (FIG. 8) of the joint head 39, such that the latter is gripped substantially free of play by the wall portions 34. The flat surfaces 40a cooperate, in the sense of a slide coupling, with the inner faces 35 or the mating flat surfaces 40b. On account of this slide coupling, the pivoting movement of the screw head 2 relative to the screw shank 3 is limited to a single axis, namely the pivot axis 18. The wall portions 34 protrude with a form fit into an area 45 of the bottom opening 16 of the screw head 2, which area 45 is widened laterally in the Z-direction and is indicated in FIG. 3 by the broken line 46. The form fit ensures that the screw shank 3 cannot turn about its central longitudinal axis 30. The radially widened area 45 is limited in the Y-direction by an outwardly curved inner wall area 47 of the head base 9 (see FIGS. 2 and 3). The mating spherical surfaces 48b on the wall of the bottom opening 16 thus extend upward and downward in the X-direction to such an extent that the joint head 39 is fixed in the direction in the screw head 2.

On the side of the joint head 39 directed toward the upper face 14 of the head, a projection 50 is present whose surface area directed toward the upper face 14 of the head is configured, at least in the middle area, as a cylindrical surface 31b, wherein the latter cooperates, in the sense of a slide coupling, with the cylindrical surface 31a present on the underside of the base 29 of the intermediate element 4. The axis of curvature 32 of the cylindrical surfaces 31a, 31b coincides with the head pivot axis 18.

By the described configuration, the cylindrical surfaces remain in contact over a large area in each pivot position of the screw head 2, such that the force applied to the clamping device 5 by the fixing screw 6 downward in the X-direction, or in the direction of the arrow 42 in FIG. 7, is introduced into the joint head 39 over a large surface area. The spherical surfaces 48a thereof are pressed against the mating spherical surfaces 48b of the head base 9, and the screw head 2 is fixed on the screw shank 3 in the respective pivot position.

The joint head 39 of the screw shank 2 and the head base 9 are connected to each other in the manner of a bayonet catch. This is achieved by the fact that the bottom opening 16 has such a cross-sectional shape that the joint head 39 can be inserted into the head base in a first position of rotation. This situation is shown in FIG. 13. The outline of the joint head 39 is indicated by the broken line 57. It will be seen that the joint head 39 can be inserted into the bottom opening 16 in the X-direction or in the direction of the central longitudinal axis 8 of the screw head. When the joint head 39 is located inside the head base 9, a rotation of the screw shank 3 through 90° in relation to the position shown in FIG. 13 results in the joint head 39 being locked in the head base 9. In this situation, the spherical surfaces 48a of the cylinder head 39 bear on the mating spherical surfaces 48b on the wall of the bottom opening (FIG. 7).

The clamping device 5 is composed of an upper clamping element 55 and a lower clamping element 56, these elements having clamping surfaces 58, 59 which, in the assembled state, extend concentrically with respect to the pivot axis 25 of the clamping device 5 and at least partially surround the hollow space 24 thereof. The diameter 72 of the hollow space 24 corresponds to the clearance 75 between the side edges 76 of the wall portions 10.

The upper clamping element 55 is rotatable on the fixing screw 6 about the central longitudinal axis 60 thereof and is otherwise axially fixed. The upper clamping element 55 also has an upper spherical surface 63a, which is directed away from the screw shank 3 and which cooperates with a mating spherical surface 63b of complementary shape on the underside of the fixing screw 6. In the assembled state, the surfaces are pressed against each other and then have a common sphere center lying on the pivot axis 25 of the clamping device 5. With the fixing screw 6 not yet fully tightened, a connection rod 15 held by the clamping elements 55, 56 can be pivoted in the X-Y plane, for example according to the double arrow 64 in FIG. 8. The pivot axis 25 of the clamping device centrally intersects the hollow space 24 thereof, at least in the assembled state, and thus extends through the central longitudinal axis 65 of the connection rod 15.

The upper clamping element 55 contains a central area 66, which is approximately circular in the plan view and which can be inserted into the recess 13, i.e. between the wall portions 10 of the screw head, of which the inner faces have a rounding corresponding to the area 66. The upper clamping element 55 is fixed in rotation in the recess 13 of the screw head 2. This ensures that, when a connection rod 15 is fixed, i.e. when the fixing screw 6 is turned into the inner thread 23 of the screw head 2, the upper clamping element 55 cannot twist and be inadvertently pressed against the connection rod 15 in this twisted position. The rotational securing of the upper clamping element 55 is achieved by two diametrically opposite and, for example, tab-shaped continuations 67 which are integrally formed on area 66 and which protrude, with a form fit acting in the circumferential direction of the screw head 2, into the gap 68 (FIGS. 2 and 3) present between the wall portions 10. The upper faces 71 of the continuations 67 extend in a common flat plane, from which the spherical surface 63a bulges forward. The continuations 67 and also the circular area 66 have side walls 69 which extend at right angles to the flat plane spanned by the upper clamping element 55 and by the upper faces 71 of the continuations, i.e. in the X-direction in the assembled state. The dimensions of the continuations 67 are such that they do not protrude from the gaps 68 present between the wall portions 10. The clamping surface 58 located on the underside of the clamping element 55 is configured matching the surface of a connection rod. It is interrupted centrally by a for example spherical recess 70. An oblong hole 73, which opens out in the upper spherical surface 63a, is present centrally in the recess 70 and in the clamping surface 58. The oblong hole 73 extends in the direction of the continuations 67 or, in the assembled state, in the Y-direction and ensures pivotability of the clamping element 55 on the fixing screw 10 (see FIG. 10). The axially fixed connection between fixing screw 6 and clamping element 55 is provided by a screw 74 that passes through the oblong hole 73. The recess 70 in the clamping element 55 has the effect that the latter, in the assembled state, has a spring action in the X-direction, which promotes the reliability of the fixing of a connection rod 15.

The lower clamping element 56 is semicircular, and the lower spherical surface 27a of the clamping device 5 is arranged on the outer face thereof directed toward the screw shank 3 in the assembled state. The free ends of the clamping element 56 are radially widened and have, on their outer face, a spherical surface 77a, which cooperates with a mating spherical surface 77b on the inner face of the wall portions 10. The spherical surfaces all extend concentrically, i.e. they have a common sphere center, the latter lying on the pivot axis 25 of the clamping device 5. The clamping element 56 is interrupted centrally by a bore 78 which extends in the direction of the central longitudinal axis 8 of the screw head 2 and which makes it easier to assemble the pedicle screw 1 from its individual parts. The clamping element 56 is fixed in rotation in the screw head 2a. This rotational fixing is ensured by the aforementioned bearing pins 7, which are inserted into lateral bores 79 extending concentrically with respect to the pivot axis 25. The bearing pins protrude in the direction from the inner faces of the wall portions 10 of the screw head 2 and each engage in an oblong hole 80 present in the free ends of the clamping element 56. The oblong hole 80 is arranged in a central position on the free ends of the clamping element 56, extends approximately in the circumferential direction thereof and opens out in a front face 83 thereof. When in a pre-assembly state in which the connection rod 15 of the clamping device 5 is not held with the final stability, because the fixing screw 6 is only slightly tightened, the clamping element 56 can be pivoted about its pivot axis 25. Since it is not yet pressed onto the mating spherical surface 27b of the intermediate element 4, this can be done with relatively little force being applied. A slight gap is present between the spherical surface 27a and the mating spherical surface 27b. In the assembled state, by contrast, the lower clamping element 56 has to be pressed firmly onto the intermediate element 4, in other words has to be moved downward in comparison with the pre-assembly state, which is ensured by the above-described support via bearing pins 7 and oblong hole 80.

The inner thread 23 of the screw head 2 and the outer thread 19 of the fixing screw 6 are configured such that the wall portions 10 are drawn radially inward when the fixing screw 6 is tightened. This is achieved by the fact that the inner thread 23 of the screw head 2 has a thread tooth 84 with a downwardly directed flank 85 and the outer thread 19 of the fixing screw 6 has a thread tooth 86 with an upwardly directed flank 87. An upwardly open acute angle α, for example of 87°, is enclosed by the former flank 85, with the central longitudinal axis 8 of the screw head 2, and by the latter flank 87, with the central longitudinal axis 60 of the fixing screw 6.

FIG. 15 shows a device which is used to stabilize the spinal column and which is composed of two connection rods 15 and a total of six pedicle screws 1. The spinal column is indicated in FIG. 15 by three schematic vertebral bodies 88. In a device of this kind, only pedicle screws 1 configured according to the invention can be used. However, it is also conceivable to use at least one pedicle screw 1 according to the invention together with monoaxial, polyaxial or other kinds of pedicle screws. Since the screw head 2 of a pedicle screw 1 is pivotable only about a single pivot axis 18, the screw head 2 can be pivoted in the direction of the double arrow 89 for example, and the screw shank 3 thus pivoted in the same direction, and in this way an incorrectly located vertebral body 88a can be repositioned.

By virtue of the fact that the upper clamping element 55 is configured such that it is fixed in rotation in the screw head 2, it can also be assigned by a tool 90, for example having a tubular element 89, to a screw head 2 in the correct position of rotation, i.e. such that the continuations 67 are inserted into the gaps present between the wall portions 10 of the screw head 2. For this purpose, the tubular element 89 has, on its inner face, two axially extending grooves 93 into which the continuations 67 of the clamping element 55 engage with a form fit.

A recess 94 is present in each of the wall portions 10 of the screw head 2. The recesses 94 lie diametrically opposite each other and a have a flat base 95. A fork-like tool can be applied to the recesses 94 in a manner fixed in rotation and, in this way, a fixing screw 1 and a vertebral body 88 connected thereto can be repositioned for example in the direction of the arrow 96 in FIG. 15.

The invention claimed is:
1. A pedicle screw, comprising:
a screw shank;
a screw head connected to said screw shank, said screw head having a central longitudinal axis extending in one direction, being an X-direction, said screw head further having an upper face, a lower end directed toward said screw shank, a head base disposed at said lower end and having a bottom opening formed therein, and two wall portions disposed on said head base and being integrally formed to extend away from said screw shank in the X-direction and laterally delimit a recess extending in a Y-direction at right angles to the X-direction and opens into said upper face of said screw head for receiving a connection rod with a circular cross-sectional shape, said wall portions each having an inner face with an inner thread;

said screw shank having a joint head protruding through said bottom opening in said head base and into said recess and mounted therein such that said screw head is pivotable relative to said screw shank about a single head pivot axis extending parallel to the Y-direction, said screw shank further having a mating cylindrical surface disposed on said joint head;

a fixing screw for fixing the connection rod in said screw head being disposed in said recess and engaging, with an outer thread, in said inner thread on said inner face of said wall portions;

a clamping device disposed between said fixing screw and said head base being held in said recess so as to be pivotable in said screw head about a pivot axis, said clamping device extending in a Z-direction at right angles to the Y-direction and X-direction and is disposed at a spacing in the X-direction above the single head pivot axis, said clamping device having a hollow space formed therein, through which the connection rod passes in an assembled state, and also a lower spherical surface directed toward said head base and said lower spherical surface having a sphere center lying on the pivot axis of said clamping device;

said clamping device, in the assembled state, being subjected by said fixing screw to a force directed toward said head base; and an intermediate element disposed in said head base, said intermediate element having a first side directed toward said clamping device, a mating spherical surface disposed on said first side and cooperating with said lower spherical surface of said clamping device and, on a second side directed toward said screw shank, said intermediate element having a cylindrical surface cooperating with said mating cylindrical surface on said joint head, wherein said cylindrical surface and said mating cylindrical surface having a common axis of curvature coincident with the single head pivot axis of said screw head.

2. The pedicle screw according to claim 1, wherein:
said head base has a wall defining complementary mating spherical surfaces; and
said joint head has two diametrically opposite spherical surfaces which cooperate, in a sense of a ball joint, with said complementary mating spherical surfaces on said wall of said head base defining said bottom opening.

3. The pedicle screw according to claim 2, wherein:
said intermediate element has walls defining mating flat surfaces; and
said joint head has two mutually parallel flat surfaces which extend in a plane spanned by the X-direction and Z-direction and which bear on correspondingly shaped and diametrically mutually opposite said mating flat surfaces on said walls of said intermediate element.

4. The pedicle screw according to claim 2, wherein said intermediate element has two downwardly protruding wall portions which are spaced diametrically apart and have mutually facing inner faces forming mating flat surfaces, wherein said downwardly protruding wall portions protrude with a form fit into a radially widened area disposed between said flat surfaces and said wall of said head base defining said bottom opening.

5. The pedicle screw according to claim 1, wherein said joint head and said head base are connected to each other by a bayonet catch.

6. The pedicle screw according to claim 5, wherein said bottom opening is shaped such that said joint head can be inserted into said head base in a first rotation position but cannot be inserted therein in a second rotation position offset through 90°, wherein said joint head has spherical surfaces disposed inside said head base and bear on mating spherical surfaces of said head base in the second rotation position.

7. The pedicle screw according to claim 1, wherein said pivot axis of said clamping device centrally intersects said hollow space in the assembled state.

8. The pedicle screw according to claim 1, wherein said clamping device has an upper clamping element and a lower clamping element which, in the assembled state, have clamping surfaces that extend concentrically with respect to said pivot axis of said clamping device and that at least partially surround said hollow space.

9. The pedicle screw according to claim 8, wherein said upper clamping element is held on said fixing screw in an axially fixed manner and is rotatable about a central longitudinal axis of said fixing screw.

10. The pedicle screw according to claim 9, wherein said upper clamping element has an upper spherical surface facing away from said screw shank, and said fixing screw has a mating spherical surface, wherein said upper spherical surface and said mating spherical surface bear on each other in the assembled state and have a common sphere center lying on said pivot axis of said clamping device.

11. The pedicle screw according to claim 8, wherein said lower clamping element has an approximately semicircular shape and an outer face directed toward said screw shank having said lower spherical surface in the assembled state.

12. The pedicle screw according to claim 11, wherein:
said screw head includes further wall portions having inner faces with mating spherical surfaces on said inner faces; and
said lower clamping element includes free ends have, on an outer face, a spherical surface for cooperating, in a sense of a slide coupling, with said mating spherical surfaces on said inner faces of said further wall portions of said screw head.

13. The pedicle screw according to claim 8, wherein said upper clamping element and said lower clamping element are held in said screw head in a rotationally fixed manner with respect to the central longitudinal axis of said screw head.

14. The pedicle screw according to claim 13, wherein said upper clamping element as two diametrically opposite continuations which, with a form fit acting in a circumferential direction of said screw head, protrude into a gap disposed between said wall portions of said screw head.

15. The pedicle screw according to claim 13, further comprising two bearing pins, said lower clamping element being held pivotably on said two bearing pins protruding from an inner face of said wall portions of said screw head.

16. The pedicle screw according to claim 15, wherein:
said lower clamping element includes free ends having an outer face with an oblong hole formed therein extending in a circumferential direction; and
said bearing pins each engage in said oblong hole.

17. The pedicle screw according to claim 1, wherein said inner thread of said screw head has a thread tooth with a downwardly facing flank, and said outer thread of said fixing screw has a thread tooth with an upwardly facing flank, wherein an upwardly opening acute angle is enclosed by said downwardly facing flank, with the central longitudinal axis of said screw head, and by said upwardly facing flank, with a central longitudinal axis of said fixing screw.

18. A device for stabilizing a spinal column, comprising:
several pedicle screws and at least one connection rod that can be fixed on the spinal column with an aid of said pedicle screws, wherein at least one of said pedicle screws is configured according to claim 1.

19. A method for stabilizing a spinal column, which comprises the steps of:
   providing several pedicle screws and at least one connection rod that can be fixed on the spinal column with an aid of the pedicle screws, wherein at least one of the pedicle screw is configured according to claim 1; and
   stabilizing the spinal column using the pedicle screws and the at least one connection rod.

* * * * *